United States Patent
Engel et al.

(10) Patent No.: US 10,081,443 B2
(45) Date of Patent: Sep. 25, 2018

(54) AIRCRAFT INSPECTION SYSTEM

(71) Applicant: Airbus Defence and Space GmbH, Taufkirchen (DE)

(72) Inventors: Franz Engel, München (DE); Daniel Bauer, Durlangen (DE); Tilman Orth, München (DE); Christian Weimer, München (DE)

(73) Assignee: Airbus Defence and Space GmbH (DE)

( * ) Notice: Subject to any disclaimer, the term of this patent is extended or adjusted under 35 U.S.C. 154(b) by 0 days.

(21) Appl. No.: 15/361,607

(22) Filed: Nov. 28, 2016

(65) Prior Publication Data

US 2017/0297745 A1    Oct. 19, 2017

(30) Foreign Application Priority Data

Nov. 27, 2015 (DE) .......... 10 2015 120 660

(51) Int. Cl.
*B64F 5/60* (2017.01)
*B64D 45/00* (2006.01)
(Continued)

(52) U.S. Cl.
CPC ............ *B64F 5/60* (2017.01); *B64D 15/20* (2013.01); *B64D 45/00* (2013.01);
(Continued)

(58) Field of Classification Search
CPC .......... B64F 5/60; B64D 45/00; B64D 15/20; H04L 67/12; G01N 21/8851; G01N 2021/8867; G01M 5/0016
See application file for complete search history.

(56) References Cited

U.S. PATENT DOCUMENTS

| | | | | |
|---|---|---|---|---|
| 4,084,427 A | * | 4/1978 | Jacoby | G01L 39/021 356/32 |
| 5,014,042 A | | 5/1991 | Michoud et al. | |
| | | (Continued) | | |

FOREIGN PATENT DOCUMENTS

| | | |
|---|---|---|
| DE | 698 05 077 T2 | 10/2002 |
| DE | 10 2011 103 003 A1 | 11/2012 |
| | (Continued) | |

OTHER PUBLICATIONS

EP 16200510.2 Search Report dated Apr. 18, 2017.

*Primary Examiner* — Russell Warren Frejd
(74) *Attorney, Agent, or Firm* — Lerner, David, Littenberg, Krumholz & Mentlik, LLP

(57) ABSTRACT

In order to provide a simplified inspection of an aircraft for the pilot, an aircraft inspection system is provided which includes at least one movable inspection unit, a position detection arrangement, and at least one data transfer interface. The at least one moveable inspection unit is moveable relative to an aircraft to be inspected. The at least one movable inspection unit includes at least one sensor for detecting a characteristic value, for verifying a characteristic and/or for determining a defect of an aircraft. The movable inspection unit is configured to generate monitoring data. When a defect or a characteristic value is detected, the position detection arrangement detects position data of the movable inspection unit in relation to the aircraft to be inspected, and assigns the position data to the monitoring data. The data transfer interface provides the position data with the assigned monitoring data as inspection data.

14 Claims, 5 Drawing Sheets

Figure 1:
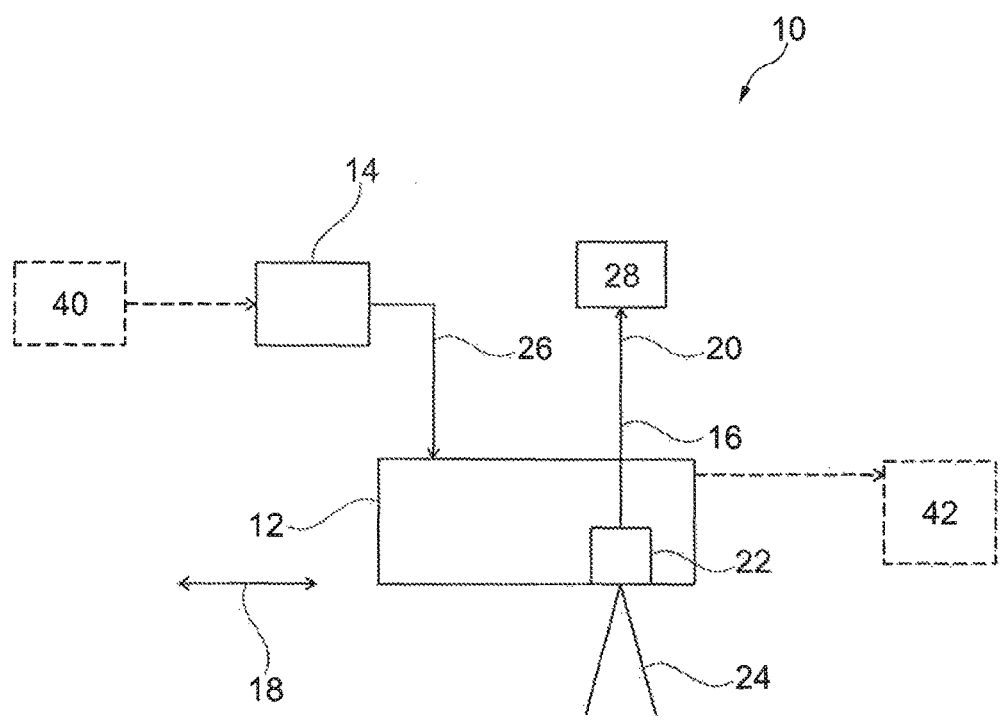

(51) Int. Cl.
  *B64D 15/20* (2006.01)
  *G01N 21/88* (2006.01)
  *G01M 5/00* (2006.01)
  *H04L 29/08* (2006.01)

(52) U.S. Cl.
  CPC ...... *G01M 5/0016* (2013.01); *G01N 21/8851* (2013.01); *G01N 2021/8867* (2013.01); *H04L 67/12* (2013.01)

(56) References Cited

U.S. PATENT DOCUMENTS

| | | |
|---|---|---|
| 5,065,630 A | 11/1991 | Hadcock et al. |
| 6,744,467 B2 | 6/2004 | Thompson et al. |
| 2010/0063650 A1 | 3/2010 | Vian et al. |
| 2010/0235037 A1 | 9/2010 | Vian et al. |
| 2012/0081540 A1 | 4/2012 | Jang |
| 2012/0140041 A1 | 6/2012 | Burgunder et al. |
| 2012/0297600 A1 | 11/2012 | Ullrich et al. |
| 2013/0018525 A1 | 1/2013 | Jang et al. |
| 2013/0126675 A1 | 5/2013 | Heppe |
| 2014/0067185 A1 | 3/2014 | Tralshawala et al. |
| 2014/0168420 A1* | 6/2014 | Naderhirn ........... G01M 5/0016 348/128 |
| 2014/0184786 A1* | 7/2014 | Georgeson ......... G01N 21/8851 348/128 |
| 2014/0300737 A1 | 10/2014 | Lust et al. |
| 2015/0302669 A1 | 10/2015 | Gonnsen et al. |
| 2016/0264262 A1* | 9/2016 | Colin ...................... B25J 5/007 |
| 2017/0154446 A1* | 6/2017 | N ............................ G06T 7/004 |

FOREIGN PATENT DOCUMENTS

| | | |
|---|---|---|
| EP | 2 345 881 A1 | 7/2011 |
| EP | 2 937 756 A1 | 10/2015 |

\* cited by examiner

AIRCRAFT INSPECTION SYSTEM

FIELD OF THE INVENTION

The present invention relates to inspection of aircraft and comprises, in particular, an aircraft inspection system, an aircraft, and a method for inspecting an aircraft.

BACKGROUND OF THE INVENTION

In connection with the operation of aircraft, for example of airplanes, regardless of the purpose of operation, for example in commercial or civil aviation, as well as in the military sector, it is required to inspect the aircraft in regular intervals to ensure that the aircraft is in a predetermined state, for example, not being damaged. A pilot of a passenger plane inspects the airplane on the ground before starting, to ensure that no damages took place during maneuvering or loading operations. Before the start procedure takes place, checks of the technical system are made from the cockpit, to check if the individual components of the aircraft work properly. However, it has become apparent that the inspection of an aircraft can be complex and time consuming.

BRIEF SUMMARY OF THE INVENTION

Thus, there may be a need to provide an inspection of an aircraft which is simpler for the pilot.

According to a first aspect of the invention, an aircraft inspection system is provided, comprising at least one movable inspection unit, a position detection arrangement and at least one data transfer interface. The at least one moveable inspection unit is moveable relative to an aircraft to be inspected. Moreover, the inspection unit comprises at least one sensor for detecting a characteristic value, for verifying a characteristic, and/or for determining a defect of an aircraft. Moreover, the inspection unit is configured to generate monitoring data. When detecting a characteristic value, verifying a characteristic, or determining a defect, the position detection arrangement detects the position data of the movable inspection unit in relation to the aircraft to be inspected. Moreover, the inspection unit assigns the position data to the monitoring data. The data transfer interface provides the position data with the assigned monitoring data in the form of inspection data.

Thereby, the pilot receives additional or alternative information about the state or condition of the aircraft to be inspected. Since the inspection unit is configured as a unit which is movable in relation to the aircraft, different characteristic values or features may be detected and by the assignment with the position data, the pilot is provided with sufficient information which allow a more precise assessment of the condition of the aircraft. This results in a relief for the pilot. Furthermore, during acquisition by the moveable inspection unit, the pilot may perform other working steps in relation with the preparation for a flight.

An aircraft may be understood, for example, as being an airplane, a helicopter, or a zeppelin.

The inspection unit may be designated as agent, for example as inspection agent.

The term "monitoring data" relates to data or data signals, which indicate a defect or a deviation from a nominal value or from a nominal state. The monitoring data comprise, for example, an actual value of a predetermined measure and or characteristic value. The monitoring data may be available, for example, as data or values, or as image data, for example photographies.

The term "position data" relates to data, on the basis of which the position in relation to the aircraft is determinable. The position data are, for example, data in a coordinate system of the aircraft. The position data may also be presented as data in a wider coordinate system, for example the coordinate system of an airport. Hence, the position data may be local or global data.

The term "inspection data" relates to data, for example for the pilot, from which data a possible present deviation emerges, together with an indication in which area of the aircraft the deviation is located.

According to an example, it is provided that the inspection unit is moveable independently or autonomously in relation to the aircraft to be inspected.

The term "independent" relates, for example, to a drive unit, which is integrated in the inspection unit, together with the necessary energy supply for the movement. The term "independently moveable" relates, for example, to the inspection unit, which is moveable in relation to the aircraft, for example by using its own drive. The inspection unit may, for example, be moved by a drive element in relation to the aircraft.

According to an example, it is provided, that the moveable inspection unit is configured to detect defects during flight operation, which are harder or not to detect in a parking position of the aircraft.

Characteristics or defects may be found, which are not detectable during the parking position.

Defects which may not be detected or which may be detected less well are, for example, deformations of constructions or deviation of material properties, which are not visible or which do not appear, respectively, while standing or while moving the aircraft on the ground, for example on the runway. For example, during flight operations a deformation of the construction may appear due to the load of the individual components as, for example, the wings, whereby, for example, smaller cracks become visible in case of deformation.

According to an embodiment, the aircraft inspection system forms an in-service inspection system.

According to an aspect, it is provided that the at least one moveable inspection unit is configured as a vehicle unit for moving inside of components of an aircraft, for detecting a characteristic value, for verifying a characteristic, and/or for determining a defect of the components from an interior side of the component.

Moving the inspection unit within the components of an aircraft enables, in particular, the detection of defects or deviations at locations, which e.g. may not be detected by an inspection by the pilot.

In an embodiment, the vehicle unit is an unmanned vehicle unit.

The term "within components" refers, e.g., to cavities or hollow spaces. For example, the inspection unit may move within a fuselage structure or wing structure, in order to be able to carry out the tests or the detection of the characteristic values from the inside. The inspection unit may, e.g., examine blades for cracks or other defects in a bypass part of an engine. The inspection unit may, e.g., also inspect cable ducts or cargo compartments.

The vehicle unit may also be used at the outer surfaces of components, in order to determine defects there.

According to an embodiment, it is provided, that the at least one movable inspection unit is designed to verify structural features during a predefined operating phase comprising, in particular, a landing phase and/or a takeoff phase, and to provide them as inspection data relating to a load condition.

This makes it possible, for example, to detect the state of the aircraft in operating phases, under which a manual inspection, for example by the pilot, is not possible at all.

For example, surface defects of a deformed structure may be detected, which defects would not be visible otherwise.

According to an aspect, it is provided that the at least one movable inspection unit is designed as an aircraft-related inspection unit in order to: i) accompany the aircraft and warn and/or prevent bird strike during a predetermined operating phase which is, in particular, a landing phase and/or a takeoff phase, and/or (ii) to control the implementation rate of de-icing.

The configuration as an aircraft-assigned or aircraft-related inspection unit, i.e. an inspection unit which is not only assigned to the aircraft, but, may also be carried by the aircraft, in particular an airplane, during operation, represents a further improvement relating to the inspection of the aircraft. The use with regard to bird strike provides an additional inspection, which is of great interest for the operation of the aircraft, especially during takeoff and landing phases. The inspection of the implementation rate of de-icing action enables a more efficient use of the provided de-icing agent, since the feedback on the implementation rate provides a more targeted application.

According to an aspect, it is provided that the at least one movable inspection unit is configured as an unmanned vehicle unit from the group of: a drone flying along the aircraft and a unit traveling (driving) along the aircraft.

The term "flying along" refers, for example, to drones, which fly along the contour of the aircraft at a predetermined distance. Drones may fly along, e.g., critical areas on an aircraft, such as the wing front edges and the aircraft nose area, i. e., the cockpit area or even the front edges of the elevator and rudder assembly.

The term "driving along" refers to units, for example, drones moving along the outer skin or along a surface in a cavity and which are in contact with the surface. For example, the term "drive" also includes running-along structures or crawling-along structures.

According to an embodiment, it is provided that the position detection arrangement comprises a position measuring system which is configured to determine internal position data within a movable coordinate system in direct relation to the aircraft and/or to determine external position data within a fixed local coordinate system in an indirect relation to the aircraft.

The term "movable coordinate system" refers, e.g., to an aircraft-related coordinate system. The term "fixed coordinate system" refers, e.g., to an airport-related or global coordinate system.

The detection of the position of the movable inspection unit takes place, e.g., by satellite positions, e.g., via GPS positioning or via GNNS data (Galileo system). The detection of the position may also be performed by high-frequency signals from external antennas for position determination, e.g., triangulation.

The position may also be captured visually via (live) camera images. The detection of the position can take place by orientation on the basis of existing features of the environment, i.e., of the airport or of the aircraft itself, e.g., by signals or images of the environment, markers on the aircraft, shape of the aircraft, etc.

According to an embodiment, it is provided that a communication arrangement is provided for the feedback of the inspection data to a pilot and/or to an operating system of the aircraft.

This enables, for example, a corresponding modification of the operation of the aircraft by taking into account the determined inspection data.

According to an embodiment, it is provided that the at least one sensor implements at least one measuring principle from the following group: thermography, laser light sectioning method, stray light method, laser time-of-flight measurement, image recognition, pattern recognition, magnetic resonance and triangulation.

According to an embodiment, it is provided that the at least one movable inspection unit comprises at least one sensor from the group of: camera, ultrasonic sensor and gas sensor (e-nose).

The camera may be designed, for example, as a high-resolution optical camera, thermal imaging camera (infrared camera), stereo camera, polarization camera, and/or UV camera.

The UV-camera can be designed with a crack infiltration spray according to an embodiment. In order to improve the visibility of cracks to the camera, a means creeping as good as possible may be provided for penetrating into the cracks, so that these can then be made visible to the camera.

According to an embodiment, it is provided that a plurality of movable inspection units is provided which cooperate with each other.

The term "cooperate" refers, e.g., to a data exchange between the inspection units. The term also includes an exchange of position information in order to simplify the acquisition of the position data.

According to one embodiment, it is provided that at least one movable inspection unit is designed as a bi-functional unit with which a determined defect may be repaired at least temporarily.

For example, the movable inspection unit may seal a detected or determined leaking point by leaving the inspection unit at the position of the leaking point.

According to a second aspect of the invention, there is also provided an aircraft comprising an operating system for operating the aircraft, and an aircraft inspection system according to one of the preceding examples. The inspection data are taken into account for the operation of the aircraft.

This enables a direct feedback of the inspection data in order to be able to carry out the operation of the aircraft in an adapted form, e.g., to avoid load peaks.

The operating system includes e.g. aerodynamic lift components and/or propulsion components which enable a flight operation. For example, the operating system includes turbines or propeller units, as well as wings with movable actuators, and also a tail unit with elevator and vertical rudder.

Thus, the aircraft with the aircraft inspection system comprises at least its own movable inspection unit assigned to the aircraft. In another example, two or more, e.g. three, four, five or more than five, e.g. ten or more inspection units are provided.

According to an embodiment, it is provided that the operating system comprises a central control unit and the inspection data are supplied to the central control unit. The central control unit adjusts the operation of the aircraft depending on the inspection data.

The aircraft inspection system may intervene into the system of the aircraft. For example, an intervention in the flight mode can occur when the aircraft inspection system detects that there is an event or a state that requires intervention. For example, after a lightning stroke upon detection of a smoke development, an extinguishing procedure may be initiated.

According to a third aspect of the invention, a method for inspecting an aircraft is provided, comprising the following steps:

a) Moving a movable inspection unit in relation to an aircraft to be inspected, wherein at least one sensor is provided for detecting a characteristic value, for verifying a characteristic, and/or for determining a defect of an aircraft;

b) Detecting a characteristic value, verifying a characteristic, and/or determining a defect by the sensor, c) Generating monitoring data;

d) Detecting position data of the movable inspection unit in relation to the aircraft to be inspected upon detection of a characteristic value, in case of a checked feature, or in the event of a determined defect;

e) Assigning the position data to the monitoring data; and f) Providing the position data with the assigned monitoring data as inspection data.

In an embodiment, it is provided that the inspection data are fed to the operating system of an aircraft in order to be able to take into account the inspection data for the operation of the aircraft.

According to an aspect, a movable unit is provided to inspect an aircraft, for example a plane. Different sensors or detection means may be used in order to be able to perform an inspection with regard to different parameters. In addition to the actual inspection, i.e. the detection of a deviating value, the position of the movable unit is also recorded in relation to the aircraft in order to link the monitoring data provided by the sensor with the position data. As a result, inspection data are available, for example, to provide the pilot with a more detailed knowledge of the state of the aircraft. In a further aspect, it is provided that an aircraft is equipped with movable units, which are, thus, assigned to the aircraft, for example an airplane. In an example the movable units may also be transported by the aircraft, if no inspection is carried out, so as to ensure that the inspection of the aircraft can be carried out independently of other infrastructural measures, for example, during a landing operation or after landing at an airport.

These and other aspects of the invention will become apparent by reference to the following explanations.

Figure 2:
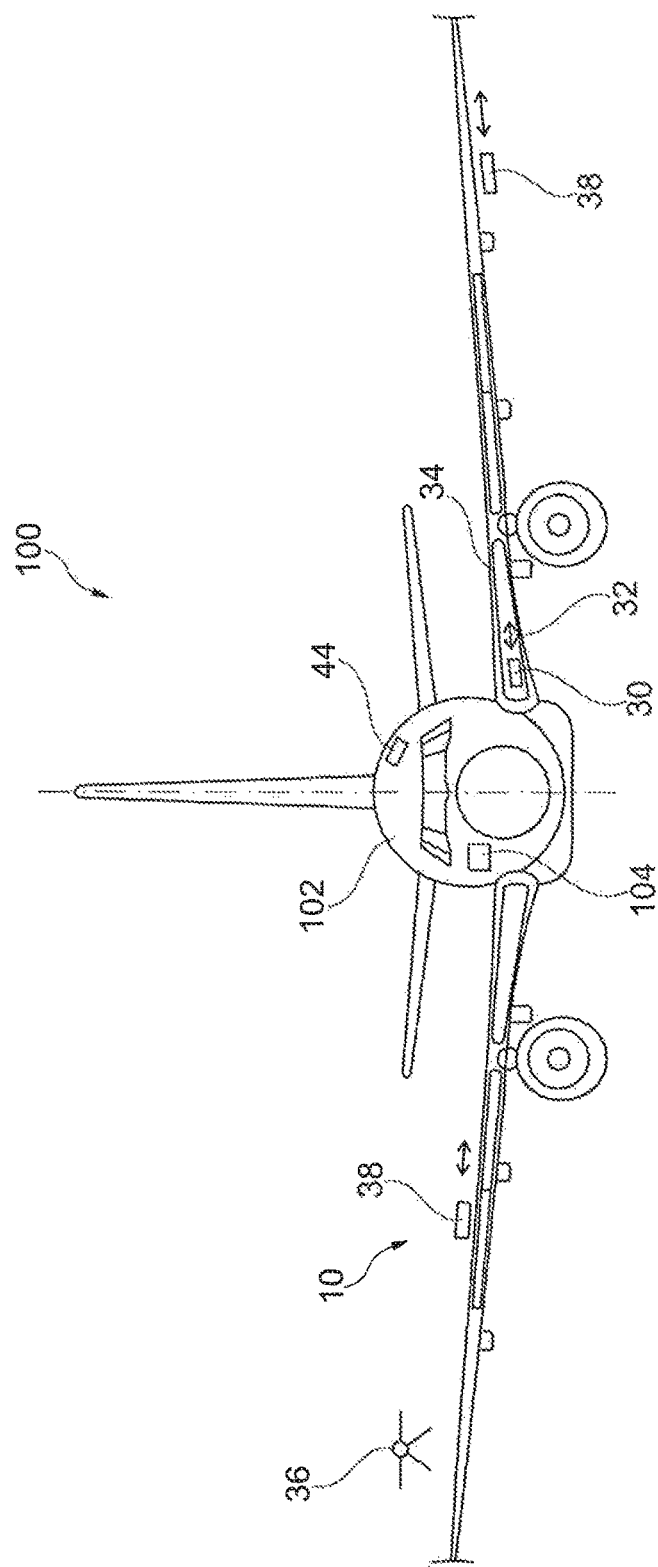
Figure 3:
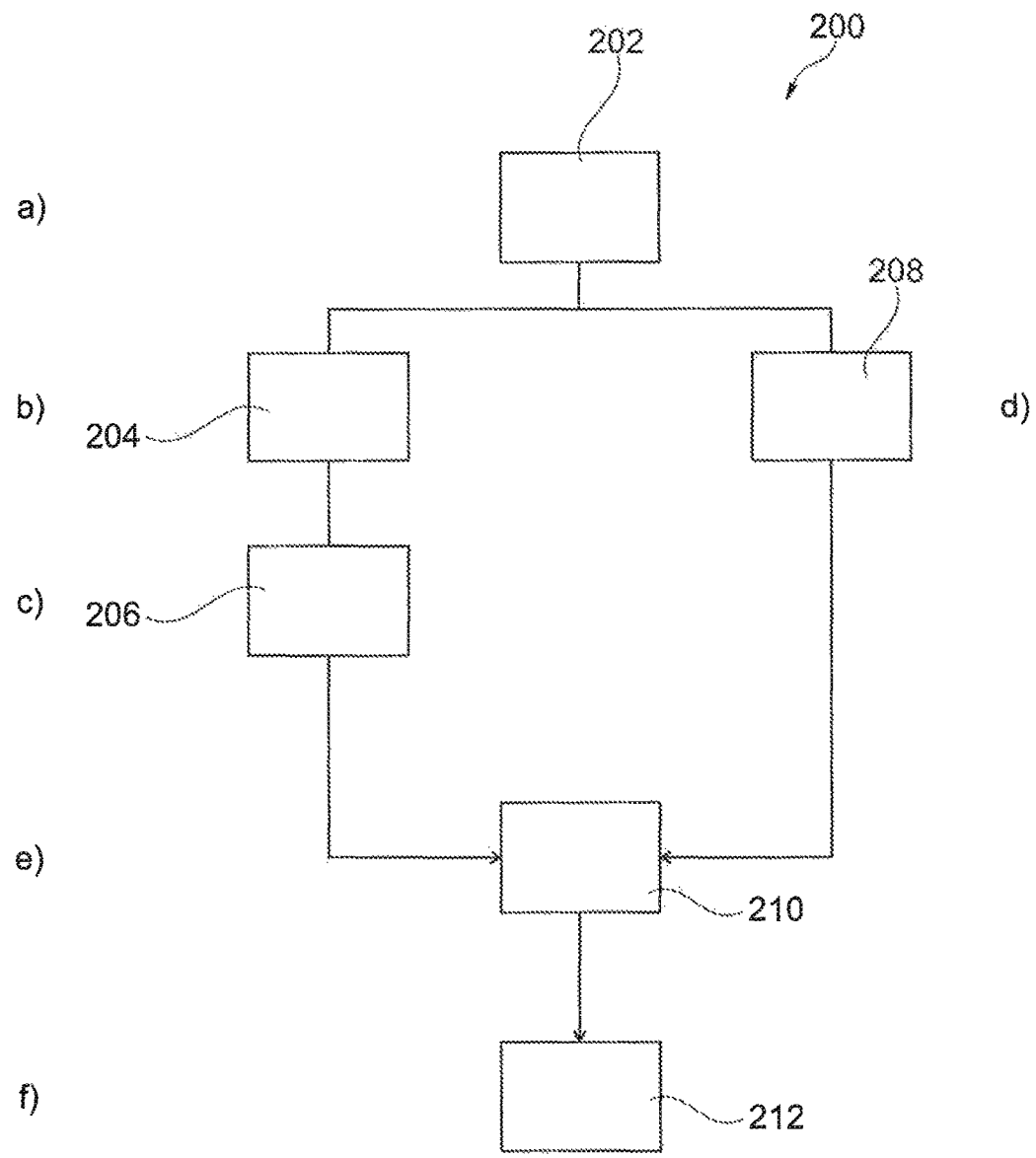
Figure 4:
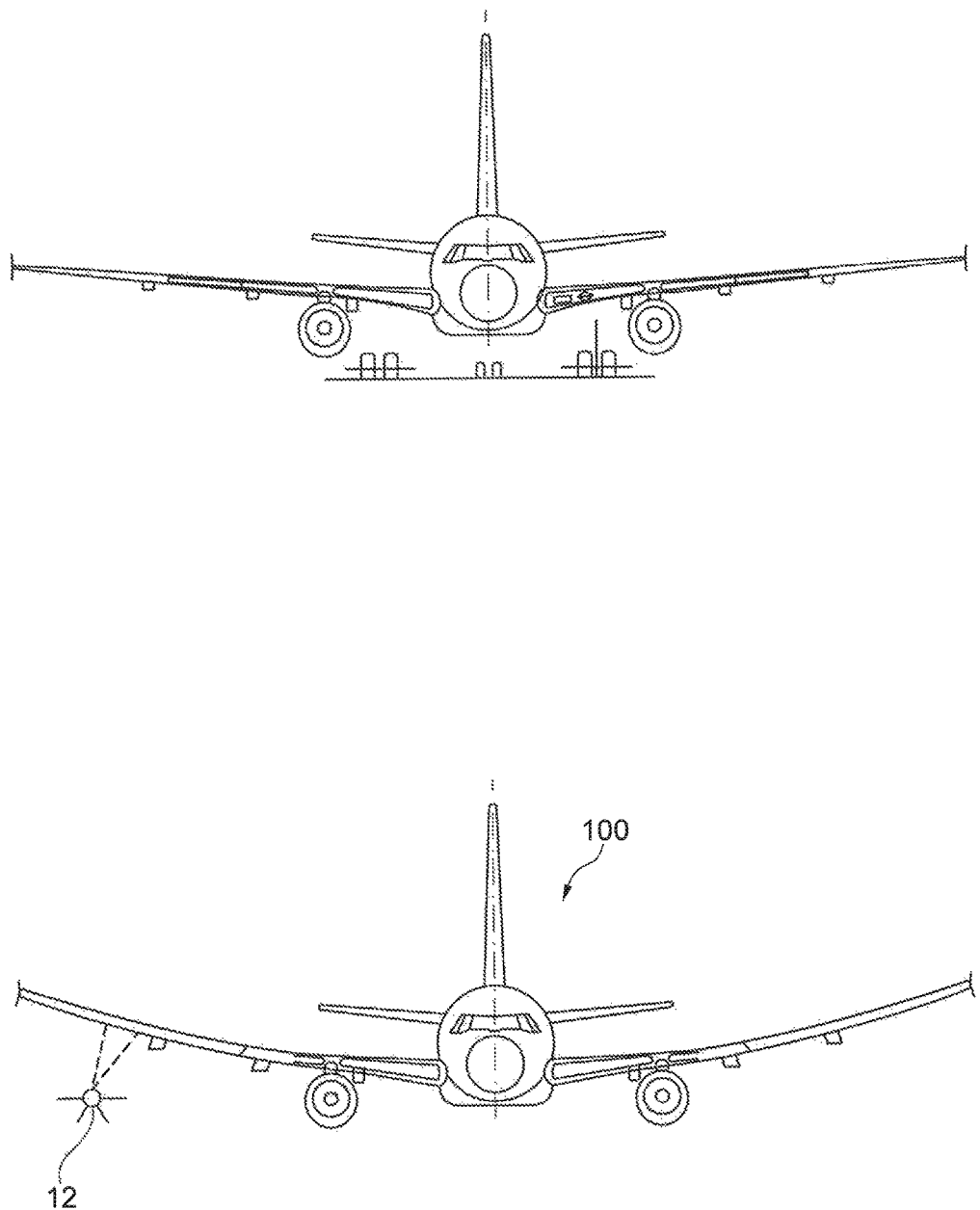
Figure 5:
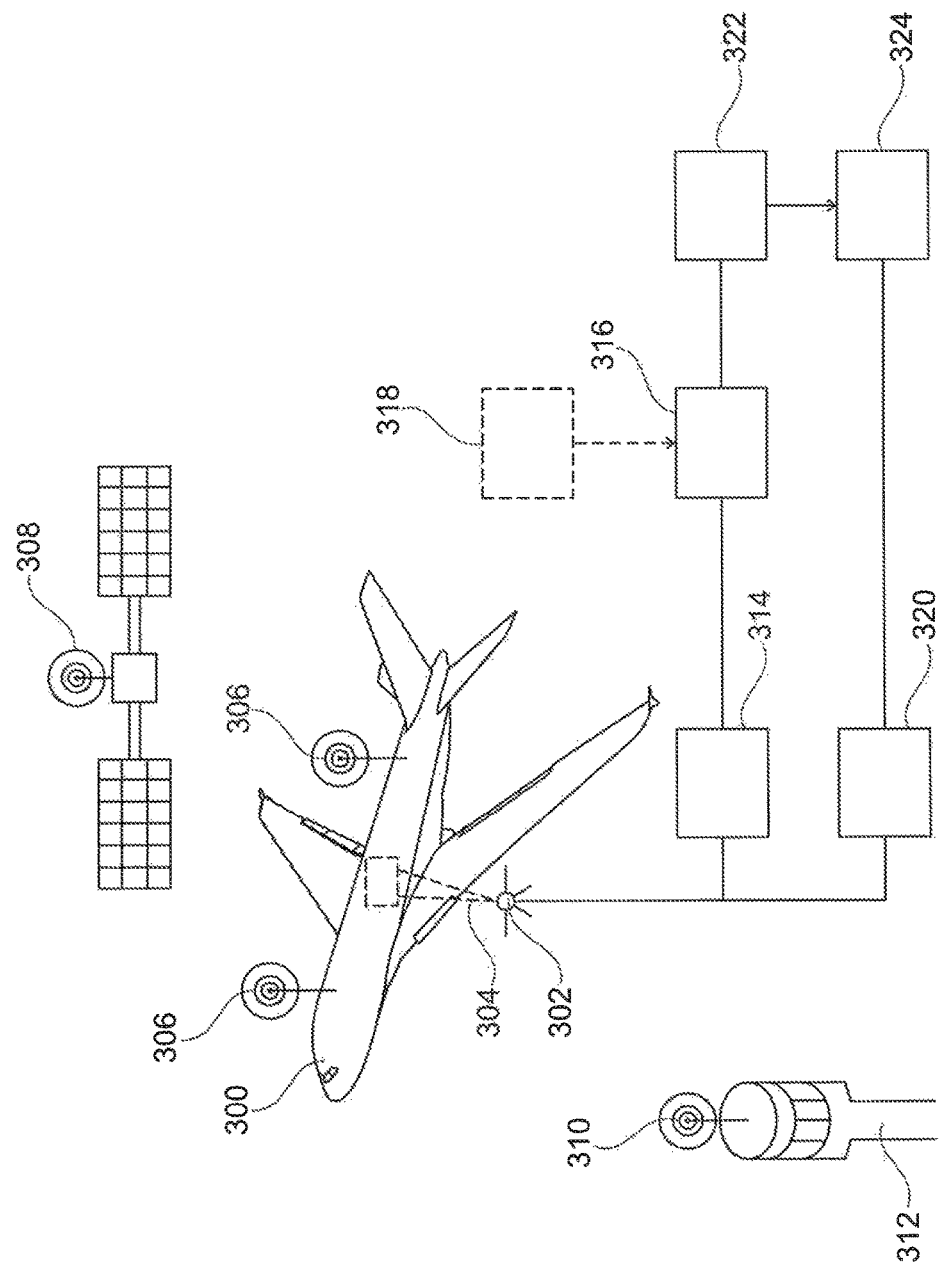

BRIEF DESCRIPTION OF THE DRAWINGS in the following, exemplary embodiments of the invention will be described in more detail with reference to the accompanying drawings. It is shown in:

FIG. 1 a schematic representation of an aircraft inspection system;

FIG. 2 an example of an aircraft in a schematic front view;

FIG. 3 an example of a method for inspecting an aircraft;

FIG. 4 a schematic representation in connection with inspecting an aircraft in an example; and FIG. 5 a schematic representation of an example of an aircraft with an aircraft inspection system.

DETAILED DESCRIPTION

FIG. 1 shows an aircraft inspection system 10 in a schematic representation. The aircraft inspection system 10 comprises at least one movable inspection unit 12 as well as a position detection arrangement 14 and at least one data transfer interface 16. The movability of the inspection unit 12 is indicated by a double arrow 18; the data transfer interface 16 is indicated with an arrow 20.

The movable inspection unit 12 is movable in relation to an aircraft to be inspected (not shown in detail in FIG. 1) and comprises at least one sensor 22. The sensor 22 is provided for detecting a characteristic value, for checking a characteristic and/or for determining a defect of an aircraft. A viewing angle symbol 24 indicates this function of the sensor 22. The movable inspection unit 12 is also adapted for generating monitoring data When a defect or a characteristic value is detected, the position detection arrangement 14 detects position data of the movable inspection unit 12 in relation to the aircraft to be inspected and assigns the position data to the monitoring data. This is indicated by an arrow 26. The data transfer interface 16 provides the position data with the assigned monitoring data as inspection data 28.

For example, the movable inspection unit 12 is designed to detect defects during flight operation, which defects are less well or not at all recognizable in a parking position of the aircraft.

In FIG. 2, it is shown in an embodiment that the at least one movable inspection unit is designed as a vehicle unit 30 for moving within components of an aircraft which is likewise shown in FIG. 2, in order to be able to carry out the detection of a characteristic value, the verification of a characteristic and/or the determination of a defect at the components from an interior side of the component.

It should be pointed out that the movability is indicated in FIG. 2 with a double arrow 32. The arrangement of the vehicle unit 30 within a wing 34 is shown by way of example only. Of course, other areas are also provided. Thus, the term "within components" includes, in particular, other cavities in the fuselage structure or wing structure, which, however, are not shown in detail in FIG. 2.

In an embodiment, it is provided that the at least one movable inspection unit 12 is configured to check structural features during a predetermined operating phase and to provide inspection data relating to a load condition, for example during landing or takeoff.

In an embodiment, which is not shown in detail, it is provided that the movable inspection unit 12 is designed as an aircraft-related inspection unit, in order, for example, to warn of or prevent bird strike during certain operating phases, e.g. during landing or takeoff. In another example, it is envisaged to be able to control the degree of de-icing action.

As a further option, it is provided that the at least one movable inspection unit is configured as an unmanned vehicle unit in the form of a drone 36 flying along the aircraft and/or as a unit 38 driving along the aircraft, both of which are shown in FIG. 2 as additional options.

In an example, it is provided that the position detection arrangement 14 comprises a position measuring system 40, which is indicated by dashed lines in FIG. 1 as a further option. For example, the position measuring system is designed to determine internal position data within a mobile coordinate system in direct relation to the aircraft. In another variant, it is provided that the position measuring system 40 is configured to determine external position data within a fixed local coordinate system in an indirect relation to the aircraft.

In a further example which is shown in FIG. 1 as a further option, it is envisaged that a communication device 42 is provided, which provides the feedback of the inspection data to a pilot and/or to an operating system of the aircraft.

The at least one sensor 22 uses as measuring principle, for example, thermography, laser light sectioning method, stray light method, laser time-of-flight measurement, image recognition, pattern recognition, magnetic resonance, and/or triangulation. For example, the sensor can be designed as a camera, ultrasonic sensor, or gas sensor, which is, however, not shown in detail.

In FIG. 2, it is indicated as an option, that a plurality of movable inspection units is present, which can be provided, for example, as differently configured unmanned units. The movable inspection units may, for example, cooperate with one another.

In a further option, it is provided that at least one movable inspection unit is designed as a bi-functional unit 44, by which a determined defect may be repaired at least temporarily. In other words, the inspection unit serves not only for detecting, but also for repairing or mitigating a determined defect.

According to a further aspect which is shown in FIG. 2, an aircraft 100 is provided comprising an operating system 102 (not shown in detail) for operating the aircraft, as well as an aircraft inspection system 10 according to one of the preceding examples. Inspection data 28 are taken into account for the operation of the aircraft.

For example, the operating system 102 comprises a central control unit 104, and the inspection data 28 are fed to the central control unit 104. The central control unit 104 adjusts the operation of the aircraft as a function of the inspection data.

In FIG. 3, an example of a method 200 for inspecting an aircraft is shown. The method 200 comprises the following steps: In a first step 202, also referred to as step a), a moveable inspection unit is moved in relation to an aircraft to be inspected. At least one sensor is provided for detecting a characteristic value, for checking a characteristic, and/or for determining a defect of the aircraft. In a second step 204, also referred to as step b), detection of a characteristic value, checking of a characteristic, and/or determination of a defect takes place by the sensor. In a third step 206, also referred to as step c), monitoring data are generated. For example, the monitoring data are generated during the detection in step b), or are a direct consequence of the detection of the characteristic values. In the second step 204, features are checked and a defect is determined additionally or alternatively. In a fourth step 208, also referred to as step d), detection of position data of the mobile inspection unit relative to the aircraft to be inspected takes place upon detection of a characteristic value, in case of a verified feature, or in case of a determined defect. Step d) is carried out, for example, at the same time as step b) or step c). In a fifth step 210, also referred to as step e), the position data are assigned to the monitoring data. In a sixth step 212, also referred to as step f), a provision of the position data with the assigned monitoring data as inspection data is provided.

In FIG. 4, an aircraft is shown schematically in an upper region in the form of an aircraft, which is located on the ground. Below, a state is shown in which the aircraft is in the air. As indicated, a deformed structure may be present in such a state. By the movable inspection unit 12, a defect may now be possibly better detected or be detected at all in this deformation state, since the defect is only visible in this state, for example on the underside of a wing, in which cracks can form in the outer skin, which cracks are only visible in the deformation state shown.

In FIG. 5, an example of an aircraft 300 is shown, in which a movable inspection unit 302 is provided to inspect the aircraft, as indicated by a dashed fan 304. In addition to the inspection, the position of the movable inspection unit 302 is recorded. For this purpose, for example, the aircraft 300 is equipped with a position detection system, which is indicated by two signal generators 306. Additionally or alternatively, the detection of the position of the movable inspection unit 302 may also take place by an indicated satellite 308, or, additionally or alternatively, via a corresponding transmitting unit 310 from the ground, for example from a tower 312 of an airport.

The movable moving unit 302 is, for example, configured to perform a feature detection 314, succeeded, for example, by a comparison 316, for which data from a database 318, for example a CAD database, can be used. In addition, a detection of defects 320 can also be provided. Inspection data 326 can thus be generated together with position detection steps 322 and 324.

In an example, it is provided that the system for data processing comprises a central data processing unit. Alternatively and additionally, the data generated by the movable inspection unit, or by a plurality of inspection units, may also be processed directly in these inspection units, i.e. be assigned to or linked with the position data.

For the movable inspection units, it is provided, in an example, that they are moved as movable units for movement within non-accessible cavities. In another example, it is provided that the movable inspection units are configured as flying drones. For example, critical areas can be flown along the aircraft and critical points can be checked or recorded by sensors or a camera. For example, for these purpose the drones can access a database that stores these types of measurements for each aircraft. The database could also be located on board of the aircraft. In another example, it is provided that the database contains information from the production of the individual components and the assembly, and this information is consulted for the detection of possible defects.

The term "drone" refers to flying devices, i.e. to unmanned flying objects, and also to moving or crawling devices, i.e. unmanned vehicles moving along a surface and being in contact therewith, for example.

In an example, it is provided that the pilot positions the drone at specific points of the aircraft to perform functional tests there, during observation by the inspection units.

The mobile inspection units may also be used to perform long-term recording of critical components, the same type of recording may, for example, be made after each landing or during each landing so as to be able to compare them over the course of time.

For positioning a drone or for orientation, it may be provided, for example, that sensors are located mounted at the drone, which sensors orientate based on existing features of the environment or of the aircraft. For this purpose, for example, position signals may be used or images of the environment may be matched. Furthermore, in an example, the airplane may be equipped with markers. In another example, the orientation is based on the shape of an aircraft recorded by a camera so that a determination of the location in relation to the aircraft can take place by matching with existing images.

In an example, it is provided that the inspection system is assigned to an airplane. In another example, it is provided, that the inspection system is an external system which is provided at the airport to inspect a plurality of airplanes. In the variant, where the inspection system is on board of the aircraft, for example, it would be possible to make the inspection data available on board of the airplane itself or the airplane would carry the data relating to itself, for example for further inspections or envisaged maintenance work.

The options described above may be combined in different ways. In particular, all options may be provided in combination; however, only individual options may be combined with one another, in deviation from the combinations shown.

The embodiments described above may be combined in different ways. In addition, it should be noted that "comprising" does not exclude other elements or steps and "a" or "an" does not exclude a plurality. It should further be noted, that features or steps which have been described with reference to one of the above embodiments, also may be used in combination with other features or steps of other exemplary embodiments described above. Reference signs in the claims should not be construed as limitation. While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. An aircraft inspection system, comprising:
   at least one movable inspection unit;
   a position detection arrangement; and
   at least one data transfer interface;
   wherein the at least one movable inspection unit:
      is configured as an unmanned vehicle unit which is movable in relation to an aircraft to be inspected during a predetermined operation phase of an aircraft, when the aircraft is not in a parking position;
      comprises at least one sensor for: detecting a characteristic value, verifying a characteristic, and/or determining a defect of the aircraft; and
      is configured to generate monitoring data,
   wherein the position detection arrangement is configured to detect position data of the movable inspection unit in relation to the aircraft to be inspected upon detection of the characteristic value, the verified feature, or the determined defect, and to assign the position data to the monitoring data, and
   wherein the data transfer interface is configured to provide the position data with the assigned monitoring data in the form of inspection data.

2. The aircraft inspection system according to claim 1, wherein the mobile inspection unit is configured to detect defects during flight operation.

3. The aircraft inspection system according to claim 1, wherein the at unmanned vehicle unit is configured for moving within components of an aircraft, for detecting the characteristic value, verifying the characteristic, and/or determining the defect in the components from an interior side of the component.

4. The aircraft inspection system according to claim 1, wherein the at least one movable inspection unit is configured to verify structural features during the predetermined operating phase, comprising a landing phase and/or a takeoff phase, and to provide the inspection data relating to a load condition.

5. The aircraft inspection system according to claim 1, wherein the at least one mobile inspection unit is configured as an aircraft-related inspection unit for at least one of:
   i) accompanying the aircraft and warn of bird strike and/or prevent bird strike during a predetermined operating phase comprising at least one of a landing phase and a takeoff phase; and
   ii) controlling an implementation rate of de-icing.

6. The aircraft inspection system according to claim 1, wherein the unmanned vehicle unit is configured as at least one of:
   a drone flying along the aircraft; and
   a unit driving along the aircraft.

7. The aircraft inspection system according to claim 1, wherein the position detection arrangement comprises a position measuring system configured for at least one of:
   determining internal position data within a mobile coordinate system in direct relation to the aircraft; and
   determining external position data within a fix local coordinate system in indirect relation to the aircraft.

8. The aircraft inspection system according to claim 1, further comprising a communication device for feedback of the inspection data to a pilot and/or an operating system of the aircraft.

9. The aircraft inspection system according to claim 1, wherein the at least one sensor is configured to implement at least one measuring principle from the following group:
   Thermography;
   Laser light sectioning method;
   Stray light method;
   Laser time-of-flight measurement;
   Image recognition;
   Pattern recognition;
   Magnetic resonance; and
   Triangulation, and
   wherein the at least one movable inspection unit comprises at least one sensor from the following group:
   Camera;
   Ultrasonic sensor; and
   Gas sensor.

10. The aircraft inspection system according to claim 1, further comprising a plurality of movable inspection units; and
   wherein the plurality of movable inspection units cooperate with each other.

11. The aircraft inspection system according to claim 1, wherein at least one movable inspection unit is configured as a bi-functional unit, by which a determined defect can be repaired at least temporarily.

12. An aircraft comprising:
   an operating system for operating the aircraft; and
   an aircraft inspection system comprising:
      at least one movable inspection unit;
      a position detection arrangement; and
      at least one data transfer interface;
      wherein the at least one movable inspection unit:
         is configured as an unmanned vehicle unit which is movable in relation to an aircraft to be inspected during a predetermined operation phase of the aircraft, when the aircraft is not in parking position;
         comprises at least one sensor for: detecting a characteristic value, verifying a characteristic, and/or determining a defect of an aircraft; and is configured to generate monitoring data;

wherein the position detection arrangement is configured to detect position data of the movable inspection unit in relation to the aircraft to be inspected upon detection of the characteristic value, the verified feature, or the determined defect, and to assign the position data to the monitoring data;

wherein the data transfer interface is configured to provide the position data with the assigned monitoring data in the form of inspection data, and wherein the inspection data are taken into account for operating the aircraft.

13. The aircraft according to claim 12, wherein the operating system comprises a central control unit;

wherein the inspection data are supplied to the central control unit; and wherein the central control unit adapts the operation of the aircraft depending on the inspection data.

14. A method for inspecting an aircraft, the aircraft being in a predetermined operation phase, when the aircraft is not in a parking position, the method comprising:
a) moving an unmanned movable inspection unit in relation to an aircraft to be inspected in the predetermined operation phase; wherein at least one sensor is provided for detecting a characteristic value, for verifying a characteristic, and/or for determining a defect of an aircraft;
b) detecting the characteristic value, verifying the characteristic, and/or determining the defect by the sensor,
c) generating monitoring data;
d) detecting position data of the movable inspection unit in relation to the aircraft to be inspected upon detecting the characteristic value, in case of the verified feature, or in the event of the determined defect;
e) assigning the position data to the monitoring data; and
f) providing the position data with the assigned monitoring data as inspection data.

* * * * *